United States Patent [19]

Haskell et al.

[11] 4,382,089

[45] May 3, 1983

[54] ANTIBACTERIAL AMIDE COMPOUNDS, COMPOSITIONS THEREOF AND METHODS OF USING THEM

[75] Inventors: Theodore H. Haskell, Ann Arbor; Marland P. Hutt, Saline, both of Mich.

[73] Assignee: Warner-Lambert Company, Morris Plains, N.J.

[21] Appl. No.: 321,019

[22] Filed: Mar. 2, 1982

[51] Int. Cl.³ ............... A61K 31/47; C07D 499/70; C07D 215/56

[52] U.S. Cl. ............... 424/258; 260/239.1; 546/156; 546/157

[58] Field of Search ............... 260/239.1; 424/258; 546/156, 157

[56] References Cited

U.S. PATENT DOCUMENTS

| | | | |
|---|---|---|---|
| 3,864,329 | 2/1975 | Tobiki et al. | 260/239.1 |
| 3,907,808 | 9/1975 | Lesher et al. | 546/156 |
| 4,263,302 | 4/1981 | Matsubara et al. | 424/258 |
| 4,267,180 | 5/1981 | Haskell et al. | 424/251 |
| 4,273,932 | 6/1981 | Matsubara et al. | 546/156 |
| 4,278,681 | 7/1981 | Haskell et al. | 260/239.1 X |

*Primary Examiner*—Natalie Trousof
*Assistant Examiner*—Vera C. Clarke
*Attorney, Agent, or Firm*—Ronald A. Daignault

[57] ABSTRACT

Novel organic amide compounds which are N-[[(acylaminoacylamino or aminoacylamino9]-dihydro-oxo-3-quinolinylcarbonyl]penicillin compounds having broad spectrum antibacterial utility are provided by (a) reacting the free amino acid of the appropriate penicillin or the acid salt or silylated derivative or complex thereof with a reactive derivative of the corresponding (acylaminoacylamino or aminoacylamino)-dihydro-oxo-3-quinolinecarboxylic acid or (b) reacting the free amino acid 6-aminopenicillanic acid or a related compound or the acid salt or silylated derivative thereof with a reactive derivative of the corresponding D-N-[(acylaminoacylamino or aminoacylamino) dihydro-oxo-3-quinolinycarbonyl]-2-substituted glycine. Pharmaceutical compositions containing said compounds and methods for treating infections using said compositions are also disclosed.

23 Claims, No Drawings

4,382,089

ANTIBACTERIAL AMIDE COMPOUNDS, COMPOSITIONS THEREOF AND METHODS OF USING THEM

SUMMARY AND DETAILED DESCRIPTION

The present invention relates to novel chemical compounds that are useful as pharmacological agents and to methods for their production. More particularly, the invention relates to novel organic amide compounds having the formula

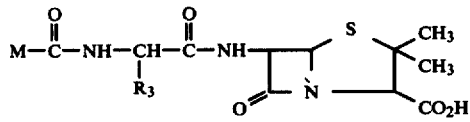

and pharmaceutically acceptable salts thereof; wherein M is

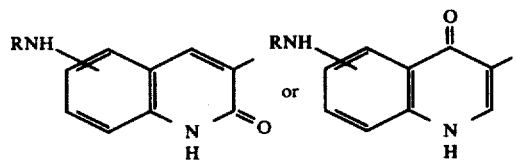

R is

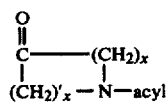

or $R_1$-[$NR_4$-acyl]$_n$; x is an integer from one to five, x' is zero, one or two; $R_1$ is hydrogen, lower alkyl, benzyl, or

wherein $R_2$ is hydrogen, amino or a lower alkyl group of from one to four carbon atoms, optionally substituted by from one to three chlorine or fluorine atoms; $R_4$ is hydrogen or lower alkyl; N-acyl is an aminoacyl moiety derived from a carboxylic acid of from two to ten carbon atoms optionally substituted by from one to three of the following groups, formamido, lower alkylamido, hydroxyl,

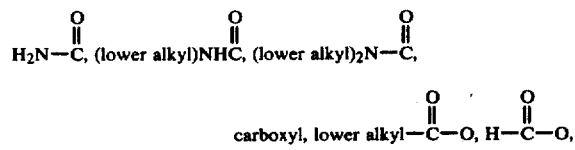

carboxyl, lower alkyl—C—O, H—C—O, amino, carbamido, carbonyl oxygen, lower alkoxy, lower alkylthio, or sulfonic acid; $R_3$ is phenyl, 4-hydroxyphenyl, 2-thienyl or cyclohexa-1,4-dien-1-yl and n is an integer of from one to four. When n is two to four, the acyl group may be the same or different. When the acyl group is substituted by more than one group, the substituents may be the same or different.

Included within the above definition for N-acyl are cyclic structures incorporating the nitrogen atom by displacement of the hydrogen atom, such as the pyroglutamyl group, prolyl group, etc.

The carbon atoms may be part of a configuration which is classified as as aliphatic, olefinic or aromatic grouping or mixture of both, such as phenethyl group.

The preferred compounds are those wherein M is

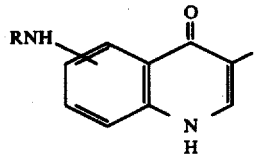

RNH is in the 6-position, R is $R_1$-[$NR_4$-acyl]$_n$, n is one and $R_3$ is 4-hydroxyphenyl.

Lower alkyl, where not specifically defined, is defined as a hydrocarbon fragment of from one to six carbon atoms. Lower alkoxy is equivalent to "lower alkyl-O—".

In accordance with the invention the foregoing amide compounds having the formula

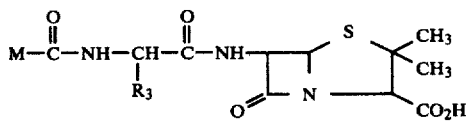

and pharmaceutically acceptable salts thereof wherein M and $R_3$ are as previously defined are produced by reacting a compound of the formula

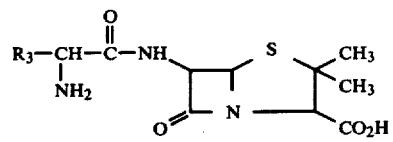

or the basic salt, silylated derivative (preferably the disilylated) or complex (preferably the dimethylsulfoxide) thereof with a reactive derivative of a 1,2-dihydro-oxo-3-quinoline carboxylic acid compound having the formula

or its acid addition salt, wherein M and $R_3$ are as previously defined.

Some examples of reactive derivatives of the substituted-dihydro-oxo-3-quinolinecarboxylic acid compound suitable for the reaction are the acid halides (especially the acid chloride), the imidazolide, mixed anhydrides (especially those from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (oxoquinoline carboxylic acid compound or penicillin compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin compounds in the free acid or salt form, aqueous solutions may be used for acylation with an acid halide or mixed anhydride under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of substituted-dihydro-2-oxo-3-quinolinecarboxylic acid compounds and acid-addition salts which are required as starting materials in the foregoing process can be prepared according to any of a variety of methods.

A substituted-dihydro-2-oxo-3-quinolinecarboxylic acid may be converted to its acid chloride utilizing thionyl chloride, its mixed anhydride utilizing ethyl chloroformate, its pentachlorophenyl ester by esterification with pentachlorophenol and its imidazolide by reacting the acid with 1,1'-carbonyldiimidazole.

Compounds of the formula

M—CO₂H wherein M is as previously defined except wherein R₁ is hydrogen are prepared by acylation of a compounds of the formulae

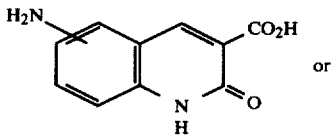

or

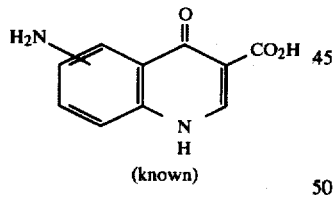

(known)

by a compound of the formula

R—OH wherein R is as previously defined except where R₁ is hydrogen.

The compound of the formula

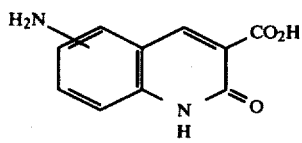

is prepared by hydrogenating of a compound of the formula

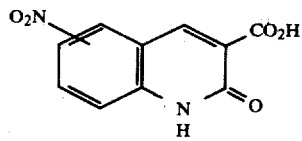

which is in turn prepared by nitration and deesterification of the known compound of the formula

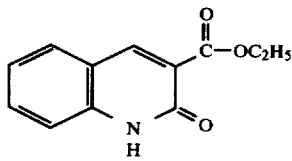

The silylated amino acid starting materials can be prepared by reacting an amino acid of the formula

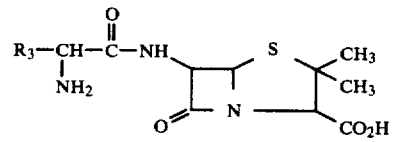

or a salt thereof wherein R₃ is as previously defined in anhydrous form with either one or two equivalents of a tri(lower alkyl)silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

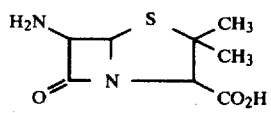

or the corresponding acid salt or silylated derivative thereof with a reactive derivative of D-N-[(substituted)-dihydro-oxo-quinolinylcarbonyl]-2-substituted glycine having the formula

or its acid addition salts where M and R₃ have the aforementioned significance.

Some examples of reactive derivatives of the D-N-(dihydro-oxo-3-quinolinylcarbonyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (quinolinyl-carboxylic acid compound or penicillanic acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 6-aminopenicillanic acid may be reacted with an acid chloride or mixed anhydride in the free acid or salt form using aqueous solutions under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of D-N-[(substituted)-dihydro-oxo-3-quinolinylcarbonyl]-2-substituted glycines or their acid-addition salts which are required as starting materials in the foregoing process cam be prepared by methods illustrated in greater detail hereinafter.

D-N-[(substituted)-dihydro-oxo-3-quinolinylcarbonyl]-2-substituted glycine compounds may be prepared by reacting the corresponding reactive derivative of said acid, such as the acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

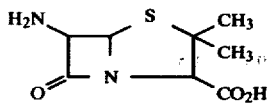

with a hexaalkyldisilazane. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention. In addition, certain of the compounds of the invention can exist in the form of an acid-addition salt. Pharmaceutically acceptable salts are formed by reaction of the free base of a carboxylate salt with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic and related acids.

When forming salts certain compounds may form mono, di, or tri, etc., salts. All of these compounds are intended to be equivalent for the purposes of the invention are intended to fall within the scope of the invention.

The compounds of the invention can exist in anhydrous form, as well as in solvated, including hydrated, forms. In general, the hydrated forms and the solvated forms with pharmaceutically acceptable solvents are equivalent to the anhydrous or unsolvated forms for the purposes of the invention.

The oxo-quinoline segment of the compounds of this invention may be capable of undergoing keto-enol tautomerism to give hydroxyquinolines. Such a tautomer is equivalent to the oxo-quinoline for the purposes of the inventions and are included within the above shown structures.

The compounds of the present invention can exist in various stereoisomeric forms. More specifically, the newly introduced amino acid fragments of the compounds may be in the form of the D-isomer, L-isomer or a mixture thereof [DL-mixture (partial or complete racemization)]. The invention is intended to include all of the isomeric forms and mixtures thereof. Even when a specific form is cited, small amounts of its stereoisomer may be present, since racemization may occur during the various steps in preparing the compound.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their nontoxic pharmaceutically acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

ACTIVITY TABLE

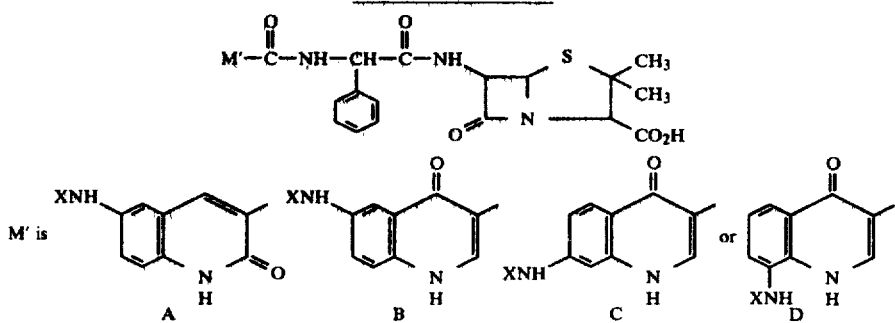

| | | Minimal Inhibitory Concentration (μg/ml) | | | | | | | | |
|---|---|---|---|---|---|---|---|---|---|---|
| | | Staph Aureus | Klebs. Pneu. | Serr. Mar. | Entero C. | Pseudo. Aeru | | E. Coli | | Prot. Vulg. |
| M 1 | X | UC-76 | MGH-2 | IMM-16 | IMM-11 | 28 | BRK | UI-18 | Brig | Vogel | 1810 |
| A | 5-oxo-pyrrolidine-2-carbonyl | 1.6 | 12.5 | 12.5 | 3.1 | 1.6 | 1.6 | 1.6 | 6.3 | 1.6 | 1.6 |
| A | CH₃C(O)—NH—CHC(O)— \| CH₃ | 1.6 | 12.5 | 12.5 | 6.3 | 1.6 | 1.6 | 1.6. | 6.3 | 1.6 | 3.1 |
| A | 1-acetyl-pyrrolidine-2-carbonyl | 0.8 | 25 | 12.5 | 3.1 | 1.6 | 1.6 | 1.6 | 3.1 | 0.2 | 0.8 |
| A | 4-hydroxy-1-acetyl-pyrrolidine-2-carbonyl | 0.8 | 25 | 25 | 6.3 | 1.6 | 3.1 | 1.6 | 12.5 | 6.3 | 3.1 |
| B | 5-oxo-pyrrolidine-2-carbonyl | 1.6 | 12.5 | 6.3 | 3.1 | 3.1 | 3.1 | 1.6 | 6.3 | 1.6 | 1.6 |
| B | CH₃CNHCHC— \| CH₃ | 1.6 | 6.3 | 3.1 | 3.1 | 0.4 | 1.6 | 1.6 | 3.1 | 0.4 | 0.8 |
| B | 1-acetyl-pyrrolidine-2-carbonyl | 3.1 | 6.3 | 6.3 | 6.3 | 3.1 | 3.1 | 3.1 | 6.3 | 0.2 | 0.8 |
| C | 5-oxo-pyrrolidine-2-carbonyl | 0.8 | 3.1 | 1.6 | 3.1 | 0.8 | 0.4 | 3.1 | 3.1 | 0.4 | 0.8 |
| C | CH₃CNHCHC— \| CH₃ | 0.8 | 6.3 | 6.3 | 3.1 | 1.6 | 1.6 | .6 | 3.1 | 0.2 | 0.8 |

ACTIVITY TABLE

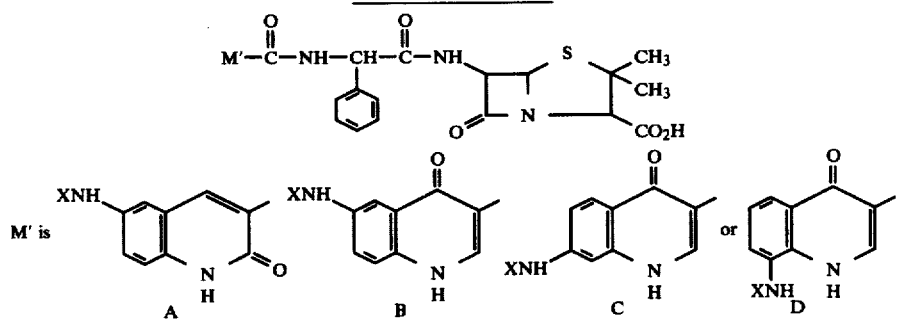

| M 1 | X | Minimal Inhibitory Concentration (μg/ml) | | | | | | | | | |
|---|---|---|---|---|---|---|---|---|---|---|---|
| | | Staph Aureus UC-76 | Klebs. Pneu. MGH-2 | Serr. Mar. IMM-16 | Entero C. IMM-11 | Pseudo. Aeru 28 BRK | Pseudo. Aeru UI-18 | E. Coli Brig | E. Coli Vogel | Prot. Vulg. 1810 |
| C | HO—[pyrrolidine with O=C-CH3, C(=O)—] | 1.6 | 12.5 | 6.3 | 6.3 | 3.1 | 3.1 | 3.1 | 12.5 | 3.1 | 0.8 |
| D | [pyrrolidinone with C(=O)—] | 1.6 | 12.5 | 12.5 | 6.3 | 0.8 | 1.6 | 3.1 | 6.3 | 3.1 | 3.1 |
| D | CH₃CNHCHC— with CH3 | 1.6 | 12.5 | 12.5 | 12.5 | 0.8 | 3.1 | .1 | 12.5 | 3.1 | 3.1 |

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg to about 1000 mg of active compound per unit dose form.

The invention is illustrated by the following examples.

STARTING MATERIALS

A. 1,2-Dihydro-6-nitro-2-oxo-3-quinolinecarboxylic acid

A solution of 10.0 g (46 mmol) of 1,2-dihydro-2-oxo-3-quinolinecarboxylic acid, ethyl ester [J. Chem. Soc., 2518 (1962)] and 50 ml of sulfuric acid is stirred in an ice bath and a cold mixture of 9.75 ml of 70% nitric acid and 9.75 ml of sulfuric acid is added dropwise over 10 minutes. The reaction solution is stirred with ice bath cooling for 1 hour and then is poured into ice and water with stirring. The resulting solid is collected by filtration and washed with water and ethanol. After drying, 10.7 g of the requisite ester is obtained, mp>310°. The structure is assigned by an unequivocal synthesis from the condensation of 2-amino-5-nitrobenzaldehyde and diethyl malonate to give the same 1,2-dihydro-6-nitro-2-oxo-3-quinolinecarboxylic acid, ethyl ester.

A mixture of 9.7 g (37 mmol) of the above ester and 200 ml of 1 N sodium hydroxide is heated on the steam bath for 1¼ hours. The resulting suspension is poured over ice and acidified with 250 ml of 1 N hydrochloric acid. The solid is collected by filtration and washed with water and ethanol to give 8.15 g the title acid, mp>310°.

B. 6-Amino-1,2-dihydro-2-oxo-3-quinolinecarboxylic acid

A solution of 3.63 g (14.9 mmol) of 1,2-dihydro-6-nitro-2-oxo-3-quinolinecarboxylic acid and 200 ml of dimethylformamide is hydrogenated using 1 g of Raney nickel catalyst at 52 psi and 23° until the required amount of hydrogen uptake is obtained. The catalyst is filtered off and the filtrate is evaporated to dryness. The residue is treated with ethanol and 3.0 g of the desired product is filtered.

| UV (pH7) | 367nm | a₁ | 257 |
|---|---|---|---|
| | 243 | | 1410 |

C. 8-Amino-1,4-dihydro-4-oxo-3-quinolinecarboxylic acid

A solution of 15.0 g (64 mmol) of 1,4-dihydro-8-nitro-4-oxo-3-quinolinecarboxylic acid [J. Amer. Chem. Soc., 68, 1264 (1946)] in 300 ml of dimethylformamide is hydrogenated using 1 g of Raney nickel catalyst at 51 psi and 23° until the required amount of hydrogen uptake is obtained. The catalyst is filtered off and the filtrate is concentrated to 50 ml and ethanol is added. The solid is collected by filtration and washed with ethanol and ether to give 9.7 g of the title compound.

| UV (pH7) | 327nm | $a_1$ | 362 |
|---|---|---|---|
| 238 | | 1370 | |

EXAMPLE 1

N-[3-[1,2-dihydro-2-oxo-6-(5-oxo-2-pyrrolidinyl)amino]-quinolinylcarbonyl]amoxicillin A mixture of 2.32 g (18 mmol) 5-oxo-L-proline, 1.39 ml (18 mmol) dimethylformamide, and 45 ml of dichloromethane is stirred at 0°–5° and 1.32 ml (18 mmol) of thionyl chloride is added. The reaction mixture is stirred at 0°–5° for 1 hour. A mixture of 2.45 g (12 mmol) of 6-amino-1,2-dihydro-2-oxo-3-quinolinecarboxylic acid, 100 ml of dichloromethane, 5.04 ml (36 mmol) triethylamine and 4.57 ml (36 mmol) chlorotrimethylsilane is stirred at room temperature for 40 min and then is cooled to 0°–5°. The solution of the acid chloride complex is added to the silylated quinoline acid and is stirred with cooling for 4 hours and at room temperature overnight. The reaction mixture is evaporated to dryness, and the residue is treated with methanol and filtered to give 2.1 g of 1,2-dihydro-2-oxo-6-[(5-oxo-2-pyrrolidinyl)amino]3-quinolinecarboxylic acid. mp>300°

$[\alpha]_D^{23} + 13.3°$ (cl, DMSO).

A mixture of 2.00 g (6.34 mmol) of the above quinoline acid, 2.06 g (12.7 mmol) of carbonyldiimidazole, and 25 ml of dimethylformamide is stirred at 42°–55° for 40 minutes and at room temperature overnight. The reaction mixture is evaporated to an oil which is treated with acetonitrile. The resulting solid is collected and washed with acetonitrile and ether to give 1.77 g of 1,2-dihydro-2-oxo-6-[(5-oxo-2-pyrrolidinyl)amino]-3-quinolinecarboxylic acid imidazolide.

A mixture of 1.72 g (4.71 mmol) of the above imidazolide, 2.88 g (4.71 mmol) of amoxicillin, 0.66 ml (4.71 mmol) of triethylamine and 25 ml of N,N-dimethylacetamide is stirred with ice bath cooling for 20 minutes and at room temperature for 4 hours. The solution is poured into 300 ml of ice and water and acidified to pH2 with 1 N hydrochloric acid. The precipitated solid is collected, suspended in water and filtered again. The solid is suspended in water and the pH is adjusted to 6.5 with 1 N sodium hydroxide, and the solution is filtered and lyophilized to give 2.38 g of the title compound as the sodium salt.

| UV (pH7) | λ362nm | $a_1^1$ | 91 | $[\alpha]_D^{23} + 38°$ (cl,pH7) |
|---|---|---|---|---|
| | 251 | | 544 | |

EXAMPLE 2

N-[6-[[(2-Acetylamino)-1-oxopropyl]amino]-1,2-dihydro-2-oxo-3-quinolinylcarbonyl]amoxicillin A mixture of 3.06 g (15 mmol) of 6-amino-1,2-dihydro-2-oxo-3-quinolinecarboxylic acid, 120 ml of dichloromethane, 6.3 ml (45 mmol) chlorotrimethylsilane and 5.7 ml (45 mmol) of triethylamine is stirred for 30 minutes at room temperature, then cooled to −50°. A mixture of 2.95 g (22.5 mmol) of N-acetyl-L-alanine, 80 ml of dichloromethane, 1.74 ml (22.5 mmol) of dimethyl formamide, and 1.65 ml (22.5 mmol) of thionyl chloride is stirred at −30° to −40° for 25 minutes. The resulting solution is added to the cold silylated quinoline and is stirred with cooling for 2 hours and at room temperature overnight. The reaction mixture is evaporated, and the residue is treated with methanol. The solid is collected to yield 1.42 g of 6-[[(2-acetylamino)-1-oxopropyl]-amino]-1,2-dihydro-2-oxo-3-quinolinecarboxylic acid.

A mixture of 1.35 g (4.25 mmol) of the above quinoline acid, 1.38 g (8.9 mmol) of carbonyldiimidazole and 15 ml of dimethylformamide is heated at 45°–48° for ½ hour and is stirred overnight at room temperature. The solution is evaporated to a gum which is treated with acetonitrile. The solid is collected to yield 1.25 g of 6-[[(2-acetylamino)-1-oxo-propyl]amino]-1,2-dihydro-2-oxo-3-quinolinecarboxylic acid imidazolide.

A mixture of 1.25 g (3.4 mmol) of the above imidazolide, 2.34 g (3.4 mmol) of amoxicillin, 0.48 ml (3.4 mmol) of triethylamine and 25 ml of N,N-dimethylacetamide is stirred with ice bath cooling for ½ hour and at room temperature for 4 hours. The solution is poured into 200 ml of ice and water and acidified to pH2 with 1 N hydrochloric acid. The solid is suspended in cold water and stirred and filtered. The solid is suspended in water, adjusted to pH6.5 with 1 N sodium hydroxide, filtered and lyophilized to give 1.89 g of the title compound as the sodium salt.

| UV (pH7) | λ364nm | $a_1^1$ | 82.8 | $[\alpha]_D^{23} + 84.1°$ (cl,pH7) |
|---|---|---|---|---|
| | 291 | | 198 | |
| | 252 | | 560 | |

EXAMPLE 3

N-[6-[[(1-Acetyl-2-pyrrolidinyl)carbonyl]amino]-1,2-dihydro-2-oxo-3-quinolinylcarbonyl]amoxicillin A solution of 4.71 g (30 mmol) of N-acetyl-L-proline and 60 ml of dichloromethane is cooled to −18° and 3.3 ml (30 mmol) of N-methyl morpholine and 3.9 ml (30 mmol) of isobutyl chloroformate is added, and the reaction mixture is stirred for 30 minutes at −10° to −20°. A mixture of 4.08 g (20 mmol) of 6-amino-1,2-dihydro-2-oxo-3-quinolinecarboxylic acid, 150 ml of dichloromethane, 8.4 ml (60 mmol) of triethylamine, and 7.6 ml (60 mmol) of chlorotrimethylsilane is stirred at room temperature for 35 minutes. The silylation mixture is cooled to −20° and the mixed anhydride of proline is added and stirred with cooling overnight. The reaction mixture is evaporated to dryness, and the residue is treated with ethanol to yield 4.42 g of 6-[[(1-acetyl-2-pyrrolidinyl)carbonyl]-amino]-1,2-dihydro-2-oxo-3-quinolinecarboxylic acid, mp 303° dec.

$[\alpha]_D^{23} - 35°$ (cl, DMSO)

A mixture of 4.34 g (12.64 mmol) of the above quinoline acid, 4.10 g (25.3 mmol) of carbonyldiimidazole, and 40 ml of dimethylformamide is stirred at 50° to 54° for 40 minutes and at room temperature overnight. The reaction solution is evaporated and the residue is treated with tetrahydrofuran to give 2.75 g of 6-[[(1-acetyl-2-pyrrolidinyl)carbonyl]amino]-1,2-dihydro-2-oxo-3-quinolinecarboxylic acid imidazolide. The addition of ether to the filtrate gives an additional 1.32 g of imidazolide.

$[\alpha]_D^{23} - 26.4°$ (cl, DMSO)

A mixture of 1.97 g (5.00 mmol) of the above imidazolide, 3.45 g (5.0 mmol) of amoxicillin, 0.70 ml (5.0 mmol) triethylamine, and 35 ml of N,N-dimethylacetamide is stirred with cooling for ½ hour and at room temperature for 1¾ hours. The solution is poured into 250 ml of ice and water and is acidified to pH2 with 1 N hydrochloric acid. The solid is filtered, resuspended in water and stirred and is filtered. The solid is suspended in water and the pH is adjusted to pH 7.0 with 1 N sodium hydroxide. The solution is filtered and lyophilized to give 2.2 g of the title compound as the sodium salt.

| UV (pH7) | λ360nm<br>252 | $a_1^1$ | 90<br>578 | $[\alpha]_D^{23}$ + 73.5° (c1,pH7) |
|---|---|---|---|---|

EXAMPLE 4

N-[6-[[(1-Acetyl-4-hydroxy-2-pyrrolidinyl)carbonyl]-amino]-1,2-dihydro-2-oxo-3-quinolinylcarbonyl]amoxicillin A mixture of 5.20 g (30 mmol) of N-acetyl-3-hydroxy-L-proline and 75 ml of dichloromethane is cooled to −15° and 3.3 ml (30 mmol) of N-methyl morpholine and 2.33 ml (30 mmol) methyl chloroformate is added and stirring is continued for 20 minutes at −10° to −20°. A mixture of 3.06 g (15 mmol) of 6-amino-1,2-dihydro-2-oxo-3-quinolinecarboxylic acid, 120 ml of dichloromethane, 6.3 ml (45 mmol) of triethylamine, and 5.7 ml (45 mmol) of chlorotrimethylsilane is stirred at room temperature for ½ hour. The silylation mixture is cooled to −20 and the cold mixed anhydride of hydroxyproline is added and stirred for 4 hours with cooling and overnight at room temperature. The reaction mixture is evaporated to an oil which is treated with acetic acid and ethanol to yield 3.92 g of 6-[[(1-acetyl-4-hydroxy-2-pyrrolidinyl)carbonyl]amino]-1,2-dihydro-2-oxo-3-quinolinecarboxylic acid.

$[\alpha]_D^{23}$ −5.0° (c1, DMSO)

A mixture of 3.85 g (10.7 mmol) of the above acid, 5.9 ml (62 mmol) of 2-methoxypropene, and 40 ml of N,N-dimethylacetamide is stirred at room temperature for 43 hours. The mixture is filtered and the filtrate is diluted with 100 ml of acetonitrile and 300 ml of ether and is stirred at room temperature for 1½ hours. The solid is filtered and washed with ether and used as is in the next reaction.

A mixture of the above 6-[[[1-acetyl-4-(1-methoxy-1-methylethoxy)2-pyrrolidinyl]carbonyl]amino]-1,2-dihydro-2-oxo-3-quinolinecarboxylic acid, 75 ml of acetonitrile, 5 ml of dimethylformamide, and 3.47 g (24.4 mmol) carbonyldiimidazole is heated at 42°-50° for ⅔ hours and is stirred for 2 hours at room temperature. The mixture is cooled with ice and stirred overnight at room temperature. The solution is concentrated to an oil and treated with tetrahydrofuran and ether, and the solid filtered to give 1.70 g of 6-[[[1-acetyl-4-(1-methoxy-1-methylethoxy)-2-pyrrolidinyl]carbonyl-]amino]-1,2-dihydro-2-oxo-3-quinolinecarboxylic acid imidazolide.

A mixture of 1.65 g (3.42 mmol) of the above imidazolide, 2.36 g (3.42 mmol) of amoxicillin, 0.48 ml (3.42 mmol) of triethylamine, and 25 ml of N,N-dimethylacetamide is stirred with ice bath cooling for 25 minutes and at room temperature for 75 minutes. The solution is cooled and 1.04 ml (3.42 mmol) of 3.3 N sodium 2-ethylhexanoate in N,N-dimethylacetamide is added. This cold solution is poured into 175 ml of ethyl acetate and the solid is filtered and washed with cold ethyl acetate and ether. The solid is dissolved with 75 ml of water and the solution is acidified to pH2 with 1 N hydrochloric acid over 1 hour with ice bath cooling. The mixture is centrifuged, and the liquid is poured off and ice water added and the mixture is centrifuged again. The liquid is poured off and the wet solid is suspended in 150 ml of water and 1 N sodium hydroxide is added to pH7.0. The solution is filtered and lyophilized to give 2.0 g of the title compound as the sodium salt.

| UV (pH7) | λ360nm<br>255 | $a_1^1$ | 85<br>562 | $[\alpha]_D^{23}$ + 86.5° (c1,pH7) |
|---|---|---|---|---|

EXAMPLE 5

N-[1,4-Dihydro-4-oxo-6[[(5-oxo-2-pyrrolidinyl)carbonyl]-amino]-3-quinolinylcarbonyl]amoxicillin A mixture of 1.94 g (15 mmol) of 5-oxo-L-proline, 1.1 ml (15 mol) dimethylformamide, and 30 ml of dichloromethane is stirred 0°-5° for 1 hour. A mixture of 2.04 g (10 mmol) of 6-amino-1,4-dihydro-4-oxo-3-quinolinecarboxylic acid, [J. Pharm. Sci., 11, 1051 (1963)] 4.2 ml (30 mmol) of triethylamine, 3.8 ml (30 mmol) of chlorotrimethylsilane, and 75 ml of dichloromethane is stirred at room temperature for 40 minutes and then is cooled at 0°. The cold acid chloride solution is added to the cold silylated quinoline and is stirred at 5° for 4 hours and overnight at room temperature. The reaction mixture is evaporated and the residue is treated with water to give 1.81 g of 1,4-dihydro-4-oxo-6-[[(5-oxo-2-pyrrolidinyl)carbonyl]-amino]-3-quinolinecarboxylic acid.

| UV (pH7) | λ309nm<br>256 | $a_1^1$ | 294<br>980 |
|---|---|---|---|

A mixture of 1.71 g (5.42 mmol) of the above quinoline acid, 1.76 g (10.85 mmol) of carbonyldiimidazole, and 25 ml of dimethylformamide is heated at 50°-55° for 45 minutes and is stirred at room temperature overnight. The reaction mixture is diluted with 150 ml acetonitrile. The solid is filtered to give 1.10 g of 1,4-dihydro-4-oxo-6-[[(5-oxo-2-pyrrolidinyl)carbonyl]amino]-3-quinolinecarboxylic acid imidazolide.

A mixture of 1.08 g (2.96 mmol) of the above imidazolide, 2.04 g (2.96 mmol) of amoxicillin, 0.42 ml (2.96 mmol) of triethylamine, and 20 ml of N,N-dimethylacetamide is stirred for 3 hours. The solution is poured into 200 ml of ice and water and 1 N hydrochloric acid is added to pH 2.5. The solid is filtered and is suspended in 100 ml of water and 1 N sodium hydroxide is added to pH 6.5. The solution is filtered and lyophilized to give 1.43 g of the title compound as the sodium salt.

| UV (pH7) | λ312nm<br>258<br>231 | $a_1^1$ | 171<br>388<br>472 | $[\alpha]_D^{23}$ + 140° (c1,pH7) |
|---|---|---|---|---|

EXAMPLE 6

N-[6-[[2-(Acetylamino)-1-oxopropyl]amino]-1,4-dihydro-4-oxo-3-quinolinylcarbonyl]amoxicillin A mixture of 1.73 g (13.2 mmol) of N-acetyl-L-alanine, 0.97 ml (13.2 mmol) of thionyl chloride, 1.02 ml (13.02 mmol) dimethylformamide, and 50 ml of dichloromethane is stirred at −20° to −30° for 20 minutes. A mixture of 2.45 g (12 mmol) of 6-amino-1,4-dihydro-4-oxo-3-quinolinecarboxylic acid, 5.04 ml (36 mmol) triethylamine, 4.57 ml (36 mmol) chlorotrimethylsilane and 100 ml of dichloromethane is stirred at room temperature for 25 minutes and is cooled to −60°. The cold acid chloride solution is added to the cold silylated quinoline and is stirred for 2 hours while the temperature comes up to 10°. The reaction mixture is evaporated to dryness and the residue is treated with water to give 2.60 g of 6-[[2-(acetylamino)-1-oxopropyl]amino]-1,4-dihydro-4-oxo-3-quinolinecarboxylic acid, mp 196°–200°.

| UV (pH7) | λ309nm | $a_1^1$ | 301 | $[\alpha]_D^{23}$ 30 40.5° (cl,DMSO) |
|---|---|---|---|---|
| | 255 | | 1050 | |

A mixture of 2.20 g (6.93 mmol) of the above quinoline acid, 2.25 g (13.9 mmol) of carbonyldiimidazole and 20 ml of dimethylformamide is stirred at 51° to 53° for 35 minutes and at room temperature overnight. The solution is diluted with 80 ml of acetonitrile and 80 ml of ether. The solid is filtered to give 2.42 g of 6-[[2-(acetylamino)-1-oxopropyl]amino)-1,4-dihydro-4-oxo-3-quinolinecarboxylic acid imidazolide.

A mixture of 2.34 g (6.37 mmol) of the above imidazolide, 4.39 g (6.37 mmol) of amoxicillin, 0.89 ml (6.37 mmol) of triethylamine, and 30 ml of N,N-dimethylacetamide is stirred with cooling for 25 minutes and at room temperature for 1½ hours. The solution is poured into 300 ml of ice and water and is acidified to pH2.4 with 1 N hydrochloric acid. The solid is filtered, suspended in water and is filtered. The solid is suspended in water and 1 N sodium hydroxide is added to pH6.5. The solution is filtered and lyophilized to give 1.68 g of the title compound as the sodium salt.

| UV (pH7) | λ313nm | $a_1^1$ | 201 | $[\alpha]_D^{23}$ + 115° (cl,pH7) |
|---|---|---|---|---|
| | 258 | | 465 | |
| | 231 | | 500 | |

EXANPLE 7

N-[6-[[(1-Acetyl-2-pyrrolidinyl)carbonyl]amino]-1,4-dihydro-4-oxo-3-quinolinylcarbonyl]amoxicillin A mixture of 7.07 g (45 mmol) of N-acetyl-L-proline, 5.85 ml (45 mmol) isobutyl chloroformate, 4.95 ml 45 mmol) N-methyl morpholine, and 90 ml of dichloromethane is stirred at −10° to −20° for 30 minutes. A mixture of 6.13 g (30 mmol) of 6-amino-1,4-dihydro-4-oxo-3-quinolinecarboxylic acid, 12.6 ml (90 mmol) triethylamine, 11.4 ml (90 mmol) chlorotrimethylsilane, and 150 ml of dichloromethane is stirred at room temperature for 30 minutes and then is cooled to −20°. The cold mixed anhydride solution is added to the cold silylated quinoline and is stirred with cooling for 4 hours and at room temperature ovenight. The reaction mixture is evaporated to dryness and the residue is treated with 1 N hydrochloric acid and the solid is filtered. The solid is digested with ethanol and filtered to give 6.43 g of 6-[[(1-acetyl-2-pyrrolidinyl)-carbonyl-]amino]-1,4-dihydro-4-oxo-quinolinecarboxylic acid.

$[\alpha]_D^{23} + 21.2°$ (cl, DMSO)

A mixture of 3.43 g (10 mmol) of the above quinoline acid, 3.24 g (20 mmol) of carbonyldiimidazole, and 40 ml of dimethylformamide is heated at 51° to 56° for 1 hour and is stirred at room temperature overnight. The reaction mixture is diluted with acetonitrile and the solid is filtered to give 3.23 g of 6-[[(1-acetyl-2-pyrrolidinyl)carbonyl]amino]-1,4-dihydro-4-oxo-quinolinecarboxylic acid imidazolide.

$[\alpha]_D^{23} + 15.8°$ (cl, DMSO)

A mixture of 2.36 g (6.0 mmol) of the above imidazolide, 4.14 g (6.0 mmol) of amoxicillin; 0.84 ml (6.0 mmol) triethylamine, and 40 ml of N,N-dimethylacetamide is stirred with cooling for 20 minutes and at room temperature for 4 hours. The reaction mixture is cooled and 1.88 ml (6.0 mmol 0 of 3.2 N sodium 2-ethyl hexanoate in N,N-dimethylacetamide is added and the solution is poured into 300 ml of ethyl acetate. The solid is filtered and dissolved with water and acidified to pH 2 with 1 N hydrochloric acid. The solid is filtered and suspended in 100 ml of water and 1 N sodium hydroxide is added to pH 6.5. The solution is filtered and lyophilized to give 4.0 g of the title compound as the sodium salt.

| UV (pH7) | λ312nm | $a_1^1$ | 387 | $[\alpha]_D^{23}$ + 116° (cl,pH7) |
|---|---|---|---|---|
| | 265 | | 870 | |
| | 260 | | 885 | |
| | 231 | | 1070 | |

EXAMPLE 8

N-[1,4-Dihydro-4-oxo-7-[[(5-oxo-2-pyrrolidinyl)carbonyl]-amino]-3-quinolinylcarbonyl]amoxicillin A mixture of 3.87 g (30 mmol) of 5-oxo-L-proline, 2.32 ml (30 mmol) of dimethylformamide, 2.19 ml (30 mmol) of thionyl chloride, and 75 ml of dichloromethane is stirred with cooling for 50 minutes. A mixture of 4.08 g (20 mmol) of 7-amino-1,4-dihydro-4-oxo-3-quinolinecarboxylic acid, [J. Amer. Chem. Soc., 69, 371 (1947)], 8.4 ml (60 mmol) of triethylamine, 7.6 ml (60 mmol) of chlorotrimethylsilane, and 200 ml of dichloromethane is stirred at room temperature for 50 minutes and then cooled to 0°. The cold acid chloride solution is added to the cold silylated quinoline and is stirred with cooling for 3 hours and at room temperature overnight. The reaction mixture is evaporated to dryness and the residue is treated with water and ethanol. The solid is filtered to give 4.72 g of 1,4-dihydro-4-oxo-7-[[(5-oxo-2-pyrrolidinyl)carbonyl]amino]-3-quinolinecarboxylic acid.

$[\alpha]_D^{23} + 13°$ (cl, DMSO)

A mixture of 4.70 g (14.9 mmol) of the above quinoline acid, 4.83 g (29.8 mmol) of carbonyldiimidazole, and 40 ml of dimethylformamide is stirred at 51°–54° for 35 minutes and at room temperature overnight. The solution is evaporated and the residue is treated with acetonitrile. The solid is filtered to give 4.60 g of 1,4-dihydro-4-oxo-7-[[(5-oxo-2-pyrrolidinyl)carbonyl]-amino]-3-quinolinecarboxylic acid imidazolide.

$[\alpha]^{23} + 5.5°$ (cl, DMSO)

A mixture of 2.19 g (6.0 mmol) of the above imidazolide, 4.14 g (6.0 mmol) of amoxicillin; 0.84 ml (6.0 mmol) of triethylamine, and 40 ml of N,N-dimethylacetamide is stirred with cooling for 30 minutes and at room temperature for 3 hours. The solution is poured into 250 ml of ice and water and is acidified to pH 2 with 1 N hydrochloric acid. The solid is filtered and suspended in 100 ml of water and 1 N sodium hydroxide is added to pH 6.5. The solution is filtered and lyophilized to give 2.70 g of the title compound as the sodium salt.

| UV (pH7) | λ247nm 237 | $a_1^1$ | 715 342 | $[\alpha]_D^{23}$ + 125° (c1,pH7) |
|---|---|---|---|---|

EXAMPLE 9

N-[7-[[2-(Acetylamino)-1-oxopropyl]amino]-1,4-dihydro-4-oxo-3-quinolinylcarbonyl]amoxicillin A mixture of 3.93 g (30 mmol) of N-acetyl-L-alanine, 3.30 ml (30 mmol) of N-methyl morpholine, 2.33 ml (30 mmol) of methyl chloroformate, and 80 ml of acetonitrile is stirred at −10° to −20° for 30 minutes. A mixture of 4.08 g (20 mmol) of 7-amino-1,4-dihydro-4-oxo-3-quinolinecarboxylic acid, 8.4 ml (60 mmol) of triethylamine, 7.6 ml (60 mmol) of chlorotrimethylsilane, and 100 ml of dichloromethane is stirred at room temperature for 30 minutes and then cooled to −20°. The cold mixed anhydride is added to the cold silylated quinoline and stirred with cooling for 3 hours and overnight at room temperature. The reaction mixture is evaporated to dryness and the residue is treated with water. The solid is filtered to give 3.98 g of 7-[[2-(acetylamino)-1-oxopropyl]-amino]-1,4-dihydro-4-oxo-3-quinolinecarboxylic acid.

$[\alpha]_D^{23}$ −0.8° (c1, DMSO)

A mixture of 2.22 g (7.0 mmol) of the above acid, 2.30 g (14.2 mmol) of carbonyldiimidazole, and 40 ml of dimethylformamide is heated at 53°-57° for 30 minutes and is stirred at room temperature overnight. The solution is diluted with 200 ml of ether. The solid is filtered to give 1.58 g of 7-[[(2-acetylamino)-1-oxopropyl]amino]-1,4-dihydro-4-oxo-3-quinolinecarboxylic acid imidazolide.

A mixture of 1.55 g (4.22 mmol) of the above imidazolide, 2.91 g (4.22 mmol) of amoxicillin; 0.59 ml (4.22 mmol) of triethylamine, and 30 ml of N,N-dimethylacetamide is stirred with cooling for 30 minutes and at room temperature for 1½ hours. The solution is cooled and 1.32 ml (4.2 mmol) of 3.2 N sodium 2-ethyl hexanoate in N,N-dimethylacetamide is added and the solution is poured into 200 ml of ethyl acetate. The solid is filtered and is dissolved with 200 ml of ice and water. The solution is acidified to pH 2.5 with 1 N hydrochloric acid. The solid is filtered and suspended in 125 ml of water and 1 N sodium hydroxide is added to pH 7.0. The solution is filtered and lyophilized to give 1.27 g of the title compound as the sodium salt.

| UV (pH7) | λ274nm 238 | $a_1^1$ | 830 333 | $[\alpha]_D^{23}$ + 130° (c1,pH7) |
|---|---|---|---|---|

EXAMPLE 10

N-[7-[[(1-Acetyl-4-hydroxy-2-pyrrolidinyl)carbonyl]-amino]-1,4-dihydro-4-oxo-3-quinolinecarbonyl]amoxicillin A mixture of 6.41 g (37 mmol) of N-acetyl-4-hydroxy-L-proline, 4.07 ml (37 mmol) of N-methyl morpholine, 2.87 ml (37 mmol) of methyl chloroformate, and 90 ml of dichloromethane is stirred at −10° to −20° for 30 minutes. A mixture of 4.08 g (20 mmol) of 7-amino-1, 4-dihydro-4-oxo-3-quinolinecarboxylic acid, 8.4 ml (60 mmol) of triethylamine, 7.6 ml (60 mmol) of chlorotrimethylsilane, and 100 ml of dichloromethane is stirred at room temperature for 30 minutes and then is cooled to −30°. The cold mixed anhydride is added to the cold silylated quinoline and is stirred with cooling for 4 hours and overnight at room temperature. The reaction mixture is evaporated to dryness and the residue is treated with water and 1 N hydrochloric acid. The solid is filtered to give 5.30 g of 7-[[(1-acetyl-4-hydroxy-2-pyrrolidinyl)carbonyl]amino]-1,4-dihydro-4-oxo-3-quinolinecarboxylic acid.

A mixture of 5.2 g (14.5 mmol) of the above quinoline acid, 7.0 ml (73 mmol) of 2-methoxypropene, and 50 ml of N,N-dimethylacetamide is stirred for 22 hours at room temperature. The solution is diluted with 100 ml of acetonitrile and 250 ml of ether and stirred for 1½ hours. The solid is filtered and used as is in the next step.

The above quinoline acid, 4.7 g (29 mmol) of carbonyldiimidazole, 25 ml of acetonitrile, and 25 ml of dimethylformamide is stirred at 44° to 52° for 40 minutes and at room temperature overnight. The mixture is diluted with 100 ml of ether and 20 ml of acetonitrile. The solid is filtered to give 2.90 g of 7-[[[1-acetyl-4-(1-methoxy-1-methylethoxy)-2-pyrrolidinyl]carbonyl]-amino]-1,4-dihydro-4-oxo-3-quinolinecarboxylic acid imidazolide.

A mixture of 2.8 g (6 mmol) of the above imidazolide, 3.8 g (6 mmol) of amoxicillin, 0.84 ml (6 mmol) of triethylamine, and 40 ml of N,N-dimethylacetamide is stirred for 20 minutes with cooling and for 2 hours at room temperature. The solution is poured into 300 ml of ice and water and acidified to pH 3 with 1 N hydrochloric acid. The mixture is stirred for 1 hour with cooling and then acidified to pH 2 and is centrifuged. The water is poured off and water is added and centrifuged again. The water is poured off and the wet solid is suspended in 150 ml of water and 1 N sodium hydroxide is added to pH 6.5. The solution is filtered and lyophilized to give 2.16 g of the title compound as the sodium salt.

| UV (pH7) | λ275nm 236 | $a_1^1$ | 625 286 | $[\alpha]_D^{23}$ + 103° (c1,pH7) |
|---|---|---|---|---|

EXAMPLE 11

N-[1,4-Dihydro-4-oxo-8-[[(5-oxo-2-pyrrolidinyl)carbonyl]-amino]-3-quinolinylcarbonyl]amoxicillin A mixture of 3.87 g (30 mmol) of 5-oxo-L-proline, 2.19 ml (30 mmol) of thionyl chloride, 2.32 ml (30 mmol) of dimethylformamide, and 75 ml of dichloromethane is stirred with cooling for 1 hour. A mixture of 4.08 g (20 mmol) 8-amino-1,4-dihydro-4-oxo-3-quinolinecarboxylic acid, 8.4 ml (60 mmol) of triethylamine, 7.6 ml (60 mmol) of chlorotrimethylsilane, and 100 ml of dichloromethane is stirred at room temperature for 40 minutes and then is cooled to 0°. The cold acid chloride solution is added to the cold silylated quinoline and the mixture is stirred with cooling for 4 hours and at room temperature overnight. The reaction mixture is evaporated to dryness and the residue is treated with ethanol to give 3.40 g of 1,4-dihydro-4-oxo-8-[[(5-oxo-2-pyrrolidinyl)carbonyl]amino]-3-quinolinecarboxylic acid.

$[\alpha]_D^{23}$ + 54° (c1, DMSO)

19

A mixture of 3.34 g (10.6 mmol) of the above quinoline acid, 3.43 g (21.2 mmol) of carbonyldiimidazole, and 30 ml of dimethylformamide is heated at 55° to 61° for 30 minutes and is stirred at room temperature overnight. The solution is concentrated and diluted with 150 ml of acetonitrile. The solid is filtered to give 2.62 g of 1,4-dihydro-4-oxo-8-[[(5-oxo-2-pyrrolidinyl)carbonyl]amino]-3-quinolinecarboxylic acid imidazolide.

A mixture of 1.83 (5.0 mmol) of the above imidazolide, 3.17 g (5.0 mmol) of amoxicillin, 0.70 ml (5.0 mmol) of triethylamine, and 30 ml of N,N-dimethylacetamide is stirred with cooling for 30 minutes and at room temperature for 4⅔ hours. The solution is poured into 250 ml of ice and water and acidified to pH 2 with 1 N hydrochloric acid. The solid is filtered and the solid is suspended in water and filtered. The solid is suspended in water and 1 N sodium hydroxide is added to pH 6.5. The solution is filtered and lyophilized to give 1.02 g of the title compound as the sodium salt.

| UV (pH7) | λ314nm | $a_1^1$ | 182 | $[\alpha]_D^{23}$ + 130° (cl,pH7) |
|---|---|---|---|---|
| | 229 | | 548 | |

EXAMPLE 12

N-[(-[[2-(Acetylamino)-1-oxopropl]amino]-1,4-dihydro-4-oxo-3-quinolinylcarbonyl]amoxicillin A mixture of 3.93 g (30 mmol) of N-acetyl-L-alanine, 3.3 ml (30 mmol) of N-methyl morpholine, 2.33 ml (30 mmol) of methyl chloroformate, and 80 ml of acetonitrile is stirred at −10° to −20° for 30 minutes. A mixture of 4.08 g (20 mmol) of 8-amino-1,4-dihydro-4-oxo-3-quinolinecarboxylic acid, 8.4 ml (60 mmol) of triethylamine, 7.6 ml (60 mmol) of chlorotrimethylsilane, and 100 ml of dichloromethane was stirred at room temperature for 40 minutes and then cooled to −20°. The cold mixed anhydride is added to the cold silylated quinoline and stirred for 4 hours with cooling and overnight at room temperature. The reaction mixture is evaporated to dryness and the residue is treated with acetonitrile and 1N hydrochloric acid. The solid is filtered to give 3.03 g of 8-[[2-(acetylamino)-1-oxopropyl]amino]-1,4-dihydro-4-oxo-3-quinolinecarboxylic acid.

$[\alpha]_D^{23}$ +26° (cl, DMSO)

A mixture of 3.00 g (9.45 mmol) of the above quinoline acid, 3.06 g (18.9 mmol) of carbonyldiimidazole, and 30 ml of dimethylformamide is heated at 54° to 57° for 30 minutes and stirred at room temperature overnight. The solution is concentrated and diluted with 200 ml of acetonitrile. The solid is filtered to give 2.15 g of 8-[[2-(acetylamino)-1-oxo-propyl]amino]-1,4-dihydro-4-oxo-3-quinolinecarboxylic acid imidazolide.

A mixture of 2.13 g (5.8 mmol) of the above imidazolide, 3.67 g (5.8 mmol) of amoxicillin, 0.81 ml (5.8 mmol) of triethylamine, and 35 ml of N,N-dimethylacetamide is stirred with cooling for 15 minutes and for 3¼ hours at room temperature. The solution is poured into 300 ml of ice and water and acidified to pH 2 with 1 N hydrochloric aci:. The mixture is centrifuged and the water is poured off. The wet solid is suspended in 200 ml of water and 1 N sodium hydroxide is added to pH 7. The solution is filtered and lyophilized to give 0.67 g of the title compound as the sodium salt.

| UV (pH7) | λ312nm | $a_1^1$ | 182 | $[\alpha]_D^{23}$ + 116° (cl,pH7) |
|---|---|---|---|---|
| | 229 | | 532 | |

We claim:
1. A compound of the formula

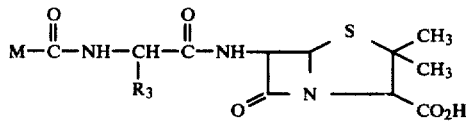

and pharmaceutically acceptable salts thereof; wherein M is

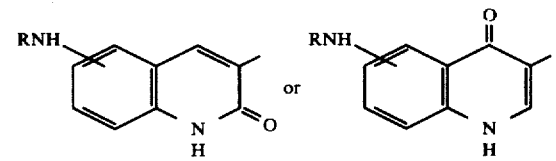

R is

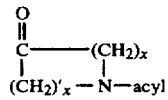

or $R_1$-[$NR_4$-acyl]$_n$; x is an integer from one to five, x' is zero, one or two; $R_1$ is hydrogen, lower alkyl, benzyl, or

wherein $R_2$ is hydrogen, amino or a lower alkyl group of from one to four carbon atoms, optionally substituted by from one to three chlorine or fluorine atoms; $R_4$ is hydrogen or lower alkyl; N-acyl is an aminoacyl moiety derived from a carboxylic acid of from two to ten carbon atoms optionally substituted by from one to three of the following groups, formamido, lower alkylamido, hydroxyl,

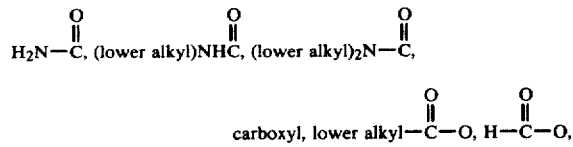

amino, carbamido, carbonyl oxygen, lower alkoxy, lower alkylthio, or sulfonic acid; $R_3$ is phenyl, 4-hydroxyphenyl, 2-thienyl or cyclohexa-1,4-dien-1-yl and n is an integer of from one to four.

2. The compounds of claim 1 wherein M is

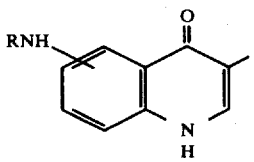

3. The compound of claim 2 wherein RNH is in the 6 or 7 -position.

4. A compound of claim 3 wherein R is $R_1[NR_4\text{-acyl}]_n$.

5. A compound of claim 4 wherein n is one.

6. A compound of claim 5 wherein $R_3$ is 4-hydroxyphenyl.

7. The compound of claim 1 having the name N-[3-[1,2-dihydro-2-oxo-6-(5-oxo-2-pyrrolidinyl)amino]-quinolinylcarbonyl]amoxicillin and pharmaceutically acceptable salts thereof.

8. A compound of claim 1 having the name N-[6-[[(2-acetylamino)-1-oxopropyl]amino]-1,2-dihydro-2-oxo-3-quinolinylcarbonyl]amoxicillin and pharmaceutically acceptable salts thereof.

9. A compound of claim 1 having the name N-[6-[[(1-acetyl-2-pyrrolidinyl)carbonyl]amino]-1,2-dihydro-2-oxo-3-quinolinylcarbonyl]amoxicillin and pharmaceutically acceptable salts thereof.

10. A compound of claim 1 having the name N-[6-[[(1-acetyl-4-hydroxy-2-pyrrolidinyl)carbonyl]amino]-1, 2-dihydro-2-oxo-3-quinolinecarbonyl]amoxicillin and pharmaceutically acceptable salts thereof.

11. A compound of claim 1 having the name N-[1,4-dihydro-4-oxo-6[[(5-oxo-2-pyrrolidinyl)carbonyl]amino]-3-quinolinylcarbonyl]amoxicillin and pharmaceutically acceptable salts thereof.

12. A compound of claim 1 having the name N-[6-[[2-(acetylamino)-1-oxopropyl]amino]-1,4-dihydro-4-oxo-3-quinolinylcarbonyl]amoxicillin and pharmaceutically acceptable salts thereof.

13. A compound of claim 1 having the name N-[6-[[(1-Acetyl-2-pyrrolidinyl)carbonyl]amino]-1,4-dihydro-4-oxo-3-quinolinylcarbonyl]amoxicillin and pharmaceuticeutically acceptable salts thereof.

14. A compound of claim 1 having the name N-[1,4-dihydro-4-oxo-7-[[(5-oxo-2-pyrrolidinyl)carbonyl]amino]-3-quinolinylcarbonyl]amoxicillin and pharmaceutically acceptable salts thereof.

15. A compound of claim 1 having the name N-[7-[[2-(Acetylamino)-1-oxopropyl]amino]-1,4-dihydro-4-oxo-3-quinolinylcarbonyl]amoxicillin and pharmaceutically acceptable salts thereof.

16. A compound of claim 1 having the name N-[7-[[(1-Acetyl-4-hydroxy-2-pyrrolidinyl)carbonyl]amino]-1,4-dihydro-4-oxo-3-quinolinylcarbonyl amoxicillin and pharmaceutically acceptable salts thereof.

17. A compound of claim 1 having the name N-[1,4-dihydro-4-oxo-8-[[(5-oxo-2-pyrrolidinyl)carbonyl]amino]-3-quinolinylcarbonyl]amoxicillin and pharmaceutically acceptable salts thereof.

18. A compound of claim 1 having the name N-[8-[[2-(Acetylamino)-1-oxopropyl]amino]-1,4-dihydro-4-oxo-3-quinolinylcarbonyl]amoxicillin and pharmaceutically acceptable salts thereof.

19. An antibacterial pharmaceutical composition comprising a compound of claim 1 in at least an effective antibacterial amount and a pharmaceutical carrier.

20. A method for treating bacterial infections in a mammal in need thereof which comprises administering thereto the pharmaceutical composition of claim 19 in an antibacterially effective amount.

21. The composition of claim 19 containing about 50 mg to about 1,000 mg of said compound per unit dose form.

22. The method of claim 20 which comprises administering about 5 mg to about 100 mg per kg of body weight per day.

23. A compound of the formula $M\text{-}CO_2H$ wherein M is

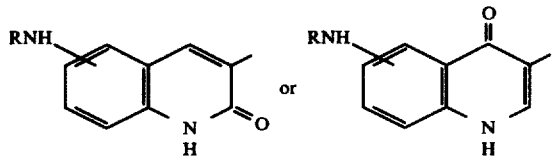

R is

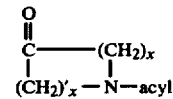

or $R_1\text{-}[NR_4\text{-acyl}]_n$; x is an integer from one to five, x' is zero, one or two; $R_1$ is hydrogen, lower alkyl, benzyl, or

wherein $R_2$ is hydrogen, amino or a lower alkyl group of from one to four carbon atoms, optionally substituted by from one to three chlorine or fluorine atoms; $R_4$ is hydrogen or lower alky; N-acyl is an aminoacyl moiety derived from a carboxylic acid of from two to ten carbon atoms optionally substituted by from one to three of the following groups, formamido, lower alkylamido, hydroxyl,

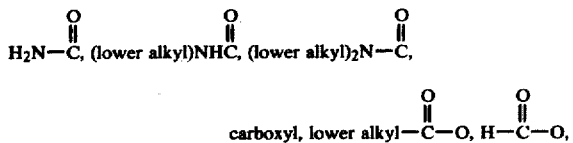

amino, carbamido, carbonyl oxygen, lower alkoxy, lower alkylthio, or sulfonic acid.

* * * * *